(12) United States Patent
Hørdum (10) Patent No.: US 9,254,373 B2
(45) Date of Patent: Feb. 9, 2016

(54) MEDICAL DEVICE COMPRISING ADHESIVE PAD

(75) Inventor: Elo Lau Hørdum, Hørsholm (DE)

(73) Assignee: UnoMedical A/S, Birkeroed (DK)

( * ) Notice: Subject to any disclaimer, the term of this patent is extended or adjusted under 35 U.S.C. 154(b) by 86 days.

(21) Appl. No.: 13/139,078

(22) PCT Filed: Dec. 18, 2009

(86) PCT No.: PCT/EP2009/067490
§ 371 (c)(1),
(2), (4) Date: Aug. 3, 2011

(87) PCT Pub. No.: WO2010/072664
PCT Pub. Date: Jul. 1, 2010

(65) Prior Publication Data
US 2011/0282293 A1   Nov. 17, 2011

(30) Foreign Application Priority Data

Dec. 22, 2008   (DK) .................................. 2008 01833

(51) Int. Cl.
*A61M 25/02*    (2006.01)
*A61M 5/142*    (2006.01)
*A61M 5/158*    (2006.01)

(52) U.S. Cl.
CPC ........... *A61M 25/02* (2013.01); *A61M 5/14248* (2013.01); *A61M 5/158* (2013.01)

(58) Field of Classification Search
CPC .. A61M 25/02; A61M 5/14248; A61M 5/158
USPC .................................. 604/174, 180, 280, 206
See application file for complete search history.

(56) References Cited

U.S. PATENT DOCUMENTS

| 1,592,462 A | 7/1926 | MacGregor |
| 2,047,010 A | 7/1936 | Dickinson |

(Continued)

FOREIGN PATENT DOCUMENTS

| DE | 4 342 329 A1 | 6/1994 |
| DE | 196 31 921 A1 | 3/1997 |

(Continued)

OTHER PUBLICATIONS

"Why inset®?" inset® infusion set product overview; http://web.archive.org/web/20040906102448/http://www.infusion-set.com/Default.asp?ID=108; two pages, Jan. 9, 2008.

(Continued)

*Primary Examiner* — Emily Schmidt
*Assistant Examiner* — Lauren M Peng
(74) *Attorney, Agent, or Firm* — Wilson Sonsini Goodrich & Rosati (57) ABSTRACT

The invention relates to an adhesive pad and a surface plate which in combination can provide a medical device which is to be placed on the skin of a patient. The combined medical device is provided with a subcutaneous part which necessitates that the device is securely and comfortably attached to the patient's skin. Often such devices are used to transfer medication such as insulin to a patient from a reservoir. An embodiment according to the invention relates to a medical device comprising—a cannula (22) or another part to be positioned subcutaneously when in use,—a surface plate (1) provided with a contact surface and with an opening (12B) through which the cannula (22) or another subcutaneously positioned part passes when the medical device is in use, and—an adhesive pad (2) secured to the contact surface of the surface plate (1) providing adhesion of the surface plate (1) to a skin surface which adhesive pad (2) comprises—a first surface facing the contact surface and having areas unreleasably secured to the contact surface by welding, and—a second surface facing the skin of a patient during use and having areas provided with a skin compatible adhesive which can be releasably secured to the skin of a patient wherein an adhesive part (30) has been placed between the contact surface of the surface plate (1) and the first surface of the adhesive pad (2) in an area where the two surfaces have not been welded together thereby securing these unwelded areas of the contact surface to the first surface.

10 Claims, 4 Drawing Sheets

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar et al. |

(56) References Cited

U.S. PATENT DOCUMENTS

| | | |
|---|---|---|
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall et al. |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,689,100 B2 * | 2/2004 | Connelly et al. ............... 604/117 |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |

(56) References Cited

U.S. PATENT DOCUMENTS

| | | |
|---|---|---|
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,137,968 B1 * | 11/2006 | Burrell et al. ............ 604/180 |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |

(56) References Cited

U.S. PATENT DOCUMENTS

| | | |
|---|---|---|
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1* | 5/2005 | Fangrow ............... A61M 5/158 604/164.01 |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1* | 3/2007 | Wright .......................... 604/500 |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1* | 3/2008 | Propp et al. ........................ 602/54 |
| 2008/0119707 A1 | 5/2008 | Stafford |
| 2008/0200897 A1 | 8/2008 | Hoss et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0118592 A1 | 5/2009 | Klitgaard |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 7/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714631 B1 | 7/1996 |
| EP | 0744183 A2 | 11/1996 |
| EP | 0747006 A1 | 12/1996 |
| EP | 0775501 B1 | 5/1997 |
| EP | 0799626 A1 | 10/1997 |
| EP | 0937475 A2 | 8/1999 |
| EP | 0956879 A1 | 11/1999 |
| EP | 2272559 A1 | 1/2001 |
| EP | 1086718 A1 | 3/2001 |
| EP | 1125593 A1 | 8/2001 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |

(56) References Cited

FOREIGN PATENT DOCUMENTS

| | | |
|---|---|---|
| EP | 1616594 A1 | 1/2006 |
| EP | 1704889 A1 | 9/2006 |
| EP | 1 719 537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| FR | 2725902 A1 | 10/1994 |
| FR | 2 752 164 A1 | 2/1998 |
| GB | 906574 | 9/1962 |
| GB | 2 088 215 A | 7/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 933 100 | 6/1982 |
| RU | 2 238 111 C2 | 12/2003 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/133702 A1 | 3/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |

(56) References Cited

FOREIGN PATENT DOCUMENTS

| WO | WO 2010/030602 A1 | 3/2010 |
|---|---|---|
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |
| WO | WO 2012/107440 A1 | 8/2012 |

OTHER PUBLICATIONS

International Search Report completed Mar. 24, 2010 for International Application No. PCT/EP2009/067490.

Written Opinion completed Mar. 24, 2010 for International Application No. PCT/EP2009/067490.

* cited by examiner

MEDICAL DEVICE COMPRISING ADHESIVE PAD

This application claims the benefit under 35 U.S.C. §371 of International Application No. PCT/EP2009/067490, filed Dec. 18, 2009, which claims the benefit of Danish Application No. PA 2008 01833, filed Dec. 22, 2008 and U.S. Provisional Application Ser. No. 61/139,833, filed Dec. 22, 2008, which are incorporated by reference herein in their entirety.

THE TECHNICAL FIELD

The invention relates to an adhesive pad and a surface plate which in combination can provide a medical device which is to be placed on the skin of a patient. The combined medical device is provided with a subcutaneous part which necessitates that the device is securely and comfortably attached to the patient's skin. Often such devices are used to transfer medication such as insulin to a patient from a reservoir.

PRIOR ART

Traditionally adhesive pads are secured to a medical device such as an infusion set by welding. Welding is highly efficient and it would not be possible to remove the adhesive pad from the medical device after the adhesive pad has been welded on to the medical device without destroying at least the adhesive pad.

WO 2006/061354 relates to a medical device comprising a transcutaneous device unit and a process unit. The transcutaneous device unit is adapted to be mounted to a skin surface of a subject and comprises a first housing, a transcutaneous device, and may comprise a flexible patch portion with an upper surface and a lower mounting surface adapted for application to the skin of a subject. The process unit comprises a second housing with a lower surface and a process assembly. The first and second housings are adapted to be secured to each other in such a way that the lower surface of the second housing is allowed to move freely relative to at least a portion of the underlying skin surface or patch. In this way a relatively flexible patch portion can adapt to the skin surface to which it is mounted both statically and dynamically without being restricted in its movements by the normally much stiffer process unit. The flexible patch portion comprise a flexible sheet (12) and a flexible support plate (11) extending from the housing, the support plate further comprises a flexible reidge formed support member (13) extending from the housing. The support plate (11) as well as the housing may be fully or partly attached to the flexible sheet e.g. by welding or adhesives.

It is though a problem that welding destroys the ability to adhere on the adhesive surface of the adhesive pad, i.e. the surface which is facing the skin of the patient after having mounted the medical device, in those areas where welding has taken place. Therefore welding is a balance between welding areas enough to secure the adhesive pad adequately to the medical device and leaving an adhesive area large enough to allow the adhesive pad to adhere adequately to the patient. The adhesive pad is considered to adhere adequately when the medical device is kept in place without moving; especially should any subcutaneously inserted parts such as cannulas or sensors be kept completely stationary until the user decides to remove the device.

One way to solve this problem is to increase the general area of the adhesive pad i.e. use an adhesive pad which is considerably larger than the surface of the medical device facing the adhesive pad. However, this approach is most convenient for smaller medical devices as the patients do not appreciate having large adhesive pads removed from their skin.

THE INVENTION

The object of the invention is to provide a medical device comprising a cannula (22) or another part to be positioned subcutaneously when in use, a surface plate (1) provided with a contact surface and with an opening (12B) through which the cannula (22) or another subcutaneously positioned part passes when the medical device is in use, and an adhesive pad (2) secured to the contact surface of the surface plate (1) providing adhesion of the surface plate (1) to a skin surface which adhesive pad (2) comprises a first surface facing the contact surface and having areas unreleasably secured to the contact surface by welding, and a second surface facing the skin of a patient during use and having areas provided with a skin compatible adhesive which can be releasably secured to the skin of a patient. The medical device further comprises an adhesive part (30) which has been placed between the contact surface of the surface plate (1) and the first surface of the adhesive pad (2) in an area where the two surfaces have not been welded together thereby securing these unwelded areas of the contact surface to the first surface.

One advantage of this inventive medical device is that it is possible to have an adhesive pad which fits e.g. an arm or another skin surface having a certain rounding perfectly, and at the same time having a relatively large rigid surface plate attached securely to the adhesive pad. This means that the patient carrying the device has an increased freedom in relation to where to position the device as the patient or the user of the device does not have to take the form of the skin surface into account when positioning the device but instead the patient can have the medical device positioned at a place where it is conveniently hidden by the clothes or conveniently positioned for other reasons.

The at least one adhesive part (30) further assures that the surface plate (1) and especially the subcutaneous part is kept in its desired subcutaneous position although parts of the surface plate are somehow distanced from the adhesive pad (2).

According to one embodiment the adhesive part (30) comprises a piece of double adhesive material i.e. each side of the adhesive part (30) is provided with adhesive coating or the adhesive part (30) comprises a coating of adhesive placed directly on the contact surface of the surface plate (1) or the adhesive part (30) comprises a coating of adhesive placed directly on the first surface of the adhesive pad (2).

According to a further embodiment an adhesive part (30) is positioned along the edge of the opening (12B) of the contact surface of the surface plate (1) through which opening (12B) the cannula (22) or another subcutaneously positioned part passes. According to this embodiment the portion of the surface plate (1) surrounding the subcutaneously positioned part is kept stationary relative to the adhesive pad and as the adhesive pad has its full adhesive strength in this area; this portion of the adhesive pad is kept stationary relative to the patient's skin. This prevents trauma of the patient's skin and increase the comfort for the patient.

According to a further embodiment the adhesive part (30) comprises a piece of double adhesive tape which can be sterilized by either gamma radiation or ethylene oxide gas.

According to a further embodiment the area covered by the adhesive part (30) is between 0.5-1.5 cm². Normally the area covered by the adhesive part (30) is around 1 cm² but the exact area depend on both the form of the adhesive part (30) and of the size of the surface plate (1) and the adhesive pad (2).

According to a further embodiment each separate welding is provided in the form of a spot welding placed on at least two opposite sides of the adhesive part (30) in order to avoid peeling i.e. separation between the surface plate 1 and the adhesive pad 2. The spot weldings are placed relatively close to the adhesive part (30) i.e. within 10 mm from the edge of the adhesive part (30).

Figure 2A:
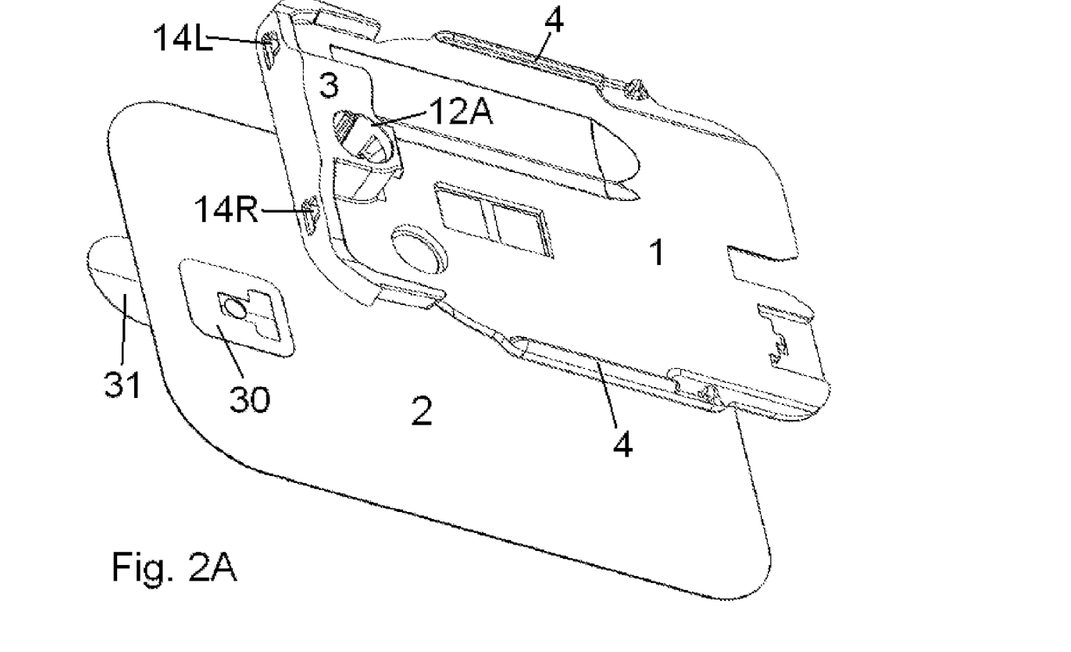
FIG. 2A-G show several embodiments of part of a medical device according to the invention having an approximately rectangular contact surface.

According to a further embodiment a welding is also placed between the adhesive part (30) and at least one edge of the surface plate 1 in order to avoid that the surface plate 1 pivots away from the adhesive pad 2 and thereby cause and inconvenience to the patient. The welding can e.g. be placed between the adhesive part (30) and at least one edge of the surface plate 1 comprising either a larger circular welding as shown in FIG. 2A-2) or several spot weldings as shown in FIG. 2E-2G.

According to a further embodiment the subcutaneously positioned part is a sensor e.g. the sensor can register the content of glucose in the blood of the patient.

A further object of the invention is to provide a base part comprising a surface plate (1) provided a contact surface and having an opening (12B) through which a cannula (22) or another subcutaneously positioned part passes when the medical device is in use, and an adhesive pad (2) secured to the contact surface of the surface plate (1) providing adhesion of the surface plate (1) to a skin surface which adhesive pad comprises a first surface facing the contact surface and having areas unreleasably secured to the contact surface by welding, and a second surface facing the skin of a patient during use and having areas provided with a skin compatible adhesive which can be releasably secured to the skin of a patient. Further, an adhesive part (30) has been placed between the contact surface of the surface plate (1) and the first surface of the adhesive pad (2) in an area where the two surfaces has not been welded together thereby optimizing the adherence between these unwelded areas of the contact surface to the first surface. "Optimizing" means that the surface plate is thoroughly secured to the adhesive pad while at the same time the surface plate can move in relation to the adhesive pad.

A further object of the invention is to provide an adhesive pad secured to a medical device and providing adhesion of the medical device to a skin surface which adhesive pad comprises a first surface facing the medical device having areas unreleasably secured to the medical device by welding, and a second surface having areas provided with a skin compatible adhesive which can be releasably secured to the skin of a patient, and also the first surface has at least one area provided with an adhesive securing the first surface to the medical device. According to this embodiment the medical device can be provided with a cannula (22) and the at least one area provided with an adhesive is surrounding the point where the cannula pass through the adhesive pad (2).

DETAILED DESCRIPTION

Embodiments of the invention will now be described with reference to the figures in which:

FIG. 1A-1C shows a prior art medical device comprising a delivery part and a base part, FIG. 1A shows the device from below, FIG. 1B shows the device seen from above and 1C shows the device in and end view opposite the views of FIGS. 1A and 1B.

FIG. 3A illustrates the prior art and FIG. 3B illustrates an embodiment according to the invention.

FIGS. 1A-C show an example of a medical device which device is relatively large and heavy. The device is of a type having credit card size, being rectangular and being self contained i.e. including a delivery part and without connections to other parts as the device carry both a reservoir and pumping and controlling means while in use.

The medical device comprises a base part which when the device is in use is secured to the skin of a patient. The base part comprises a surface plate 1 and an adhesive pad 2 which adhesive pad 2 is unreleasably fastened to the surface plate 1 during manufacturing of the medical device. A connection part 3 is attached to the surface plate 1 which surface plate 1 can be constructed of a molded plastic material. The connection part 3 comprises a fluid path provided with a membrane 17 and a delivery part comprising a reservoir 6, the two parts are in a position where they are separated from each other and they are shown from different angles. In FIG. 1A the two parts are shown from below. This view shows an opening 12B through which a cannula part 7 can be inserted through the base part and through which opening 12B a cannula 22 extends. The connection part 3 is provided with a cannula opening 12A which accurately fits around a cannula part 7 when the cannula part 7 is mounted in the connection part 3 i.e. the cannula opening 12A has the same shape or profile as the cannula part 7 and is just big enough to let the cannula part 7 pass through and then fit into the opening.

The surface plate 1 has a contact surface which is defined as the surface which is in contact with the proximal or the first surface of the adhesive pad 2 which is the surface of the adhesive pad 2 facing the medical device. The contact surface of the surface plate and the first side of the adhesive pad 2 has areas unreleasably secured to each other by welding. Further the second surface of the adhesive pad 2 i.e. the surface facing the skin of the patient has areas provided with a skin compatible adhesive. Normally the full surface of the second surface will be adhesive except for the areas which have been subjected to welding when joining the surface plate 1 and the adhesive pad 2 together.

Figure 2B:
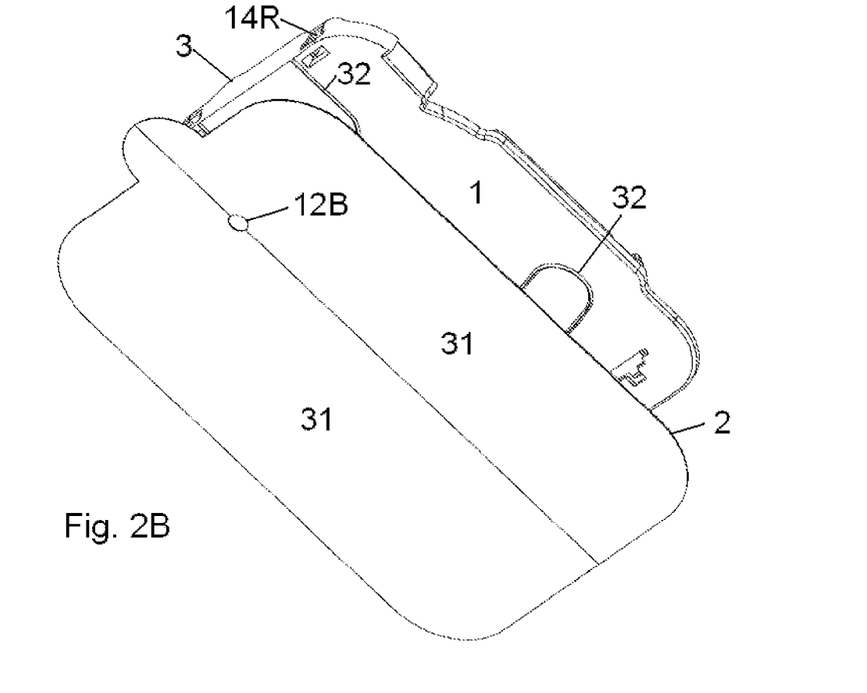
Figure 2C:
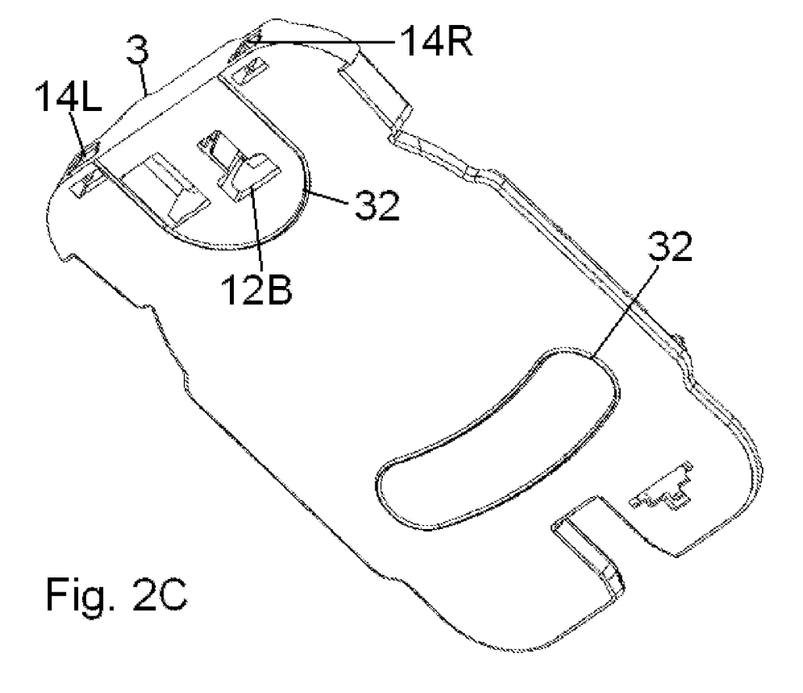
Figure 2D:
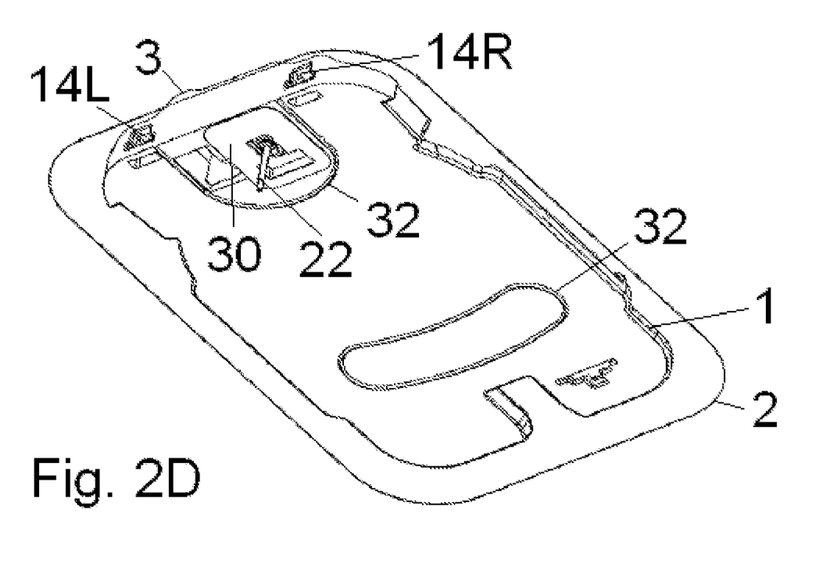
Figure 2E:
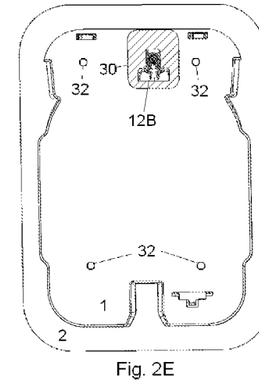
Figure 2F:
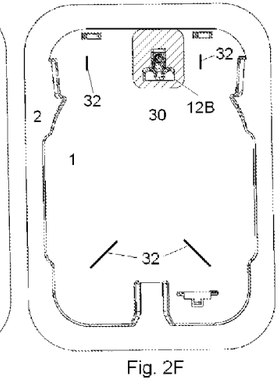
Figure 2G:
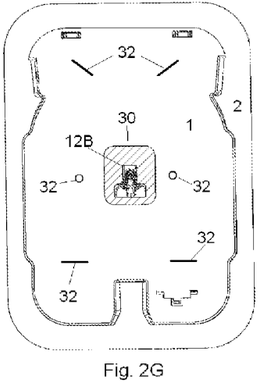

In FIG. 2B the cannula part 7 is shown in a position where the cannula part 7 is fully inserted. When the cannula part 7 is fully inserted, the upper surface i.e. the distal surface of the cannula part 7 is normally at level with or at a lower level than the outer surface of the connection part 3 around the cannula opening 12A. From this view it is possible to see how the reservoir 6 is positioned in the delivery part 8 and to see how two opposite positioned release handles 9 are placed at the edge of the delivery part 8. Further a longitudinal track corresponding to longitudinal raised guiding means 4 on the base part can be seen.

The two release handles 9 are formed as s-shaped bands where one end is fastened hinge-like to the housing of the delivery part 8 and the first curve in the s-shape is slightly extending the outer surface of the housing of the delivery part whereas the second curve is free i.e. not attached to the housing of the delivery part 8 and is provided with a hook-like shape which can fold around a part 15 protruding from the distal surface of the base part. When the delivery part is locked to the base part both release handles 9 are folded round a protruding part 15, when the delivery part 8 is to be removed from the base part, the two opposite release handles 9 are pushed together whereby the hook-like parts of the release handles 9 are released from the protruding parts 15 of the base part, and the delivery part can be moved backwards i.e. in the direction away from the cannula part 7 and removed from the base part in this direction.

In FIG. 1B the two parts are shown from above. This view shows how the delivery part 8 of this embodiment can be joined to the base part by pushing the delivery part 8 down toward the guiding means 4 which in this case is a longitudinal raised platform having e.g. a metal lining 5 fastened to the top surface. The delivery part 8 is provided with corresponding means e.g. comprising a track corresponding to the raised platform 4. The corresponding means of the delivery part 8 can slide along the metal lining 5 of the raised platform 4 of the base part in the longitudinal direction. When the delivery part 8 arrives at its working position, the two release handles 9 engage respectively with the two protruding parts 15 protruding from the upper surface of the surface plate 1. When the delivery part 8 is in its working position it is locked in any horizontal direction by the release handles 9. The locking mechanisms make it possible to fasten and release the delivery device from the base part as often as needed i.e. a single-use base part can be combined with a multi-use delivery part.

In FIG. 1C the two parts are shown from the end opposite of where the inserter was fastened before insertion of the penetrating member. From this side it is possible to see the inlet opening 13 in the connection part 3 through which e.g. medication from the reservoir 6 can enter, the inlet opening 13 is protected with a membrane to prevent contamination with microorganisms. The connection part 3 can be provided with both a connector needle (not shown as it is placed behind the bubble shaped membrane 17) and a bubble shaped self closing membrane 17 and the reservoir 6 can be provided with a bubble shaped self closing membrane. Hereby a fluid path is established providing transfer of medication e.g. insulin or nutrients from the reservoir to the connector part 3. As both parts are provided with self closing membranes it will be possible to separate the two units from each other and rejoin them at a later time without the connection part 3 and thereby the patient being contaminated.

FIGS. 2A-G show embodiments of a medical device according to the invention having an approximately rectangular contact surface embodiment attached to an adhesive pad. The adhesive pad 2 of FIG. 2A-G and the illustrated attachments can e.g. be used together with a surface plate 1 and a delivery device of the type shown in FIG. 1A-C.

The base part shown in FIG. 2A-D is a second embodiment differing from the embodiment shown in FIG. 1A-C in that e.g. the guiding means 4 of the surface plate 1 comprises two elongated bars placed along opposite sides of the base part.

Figure 1:
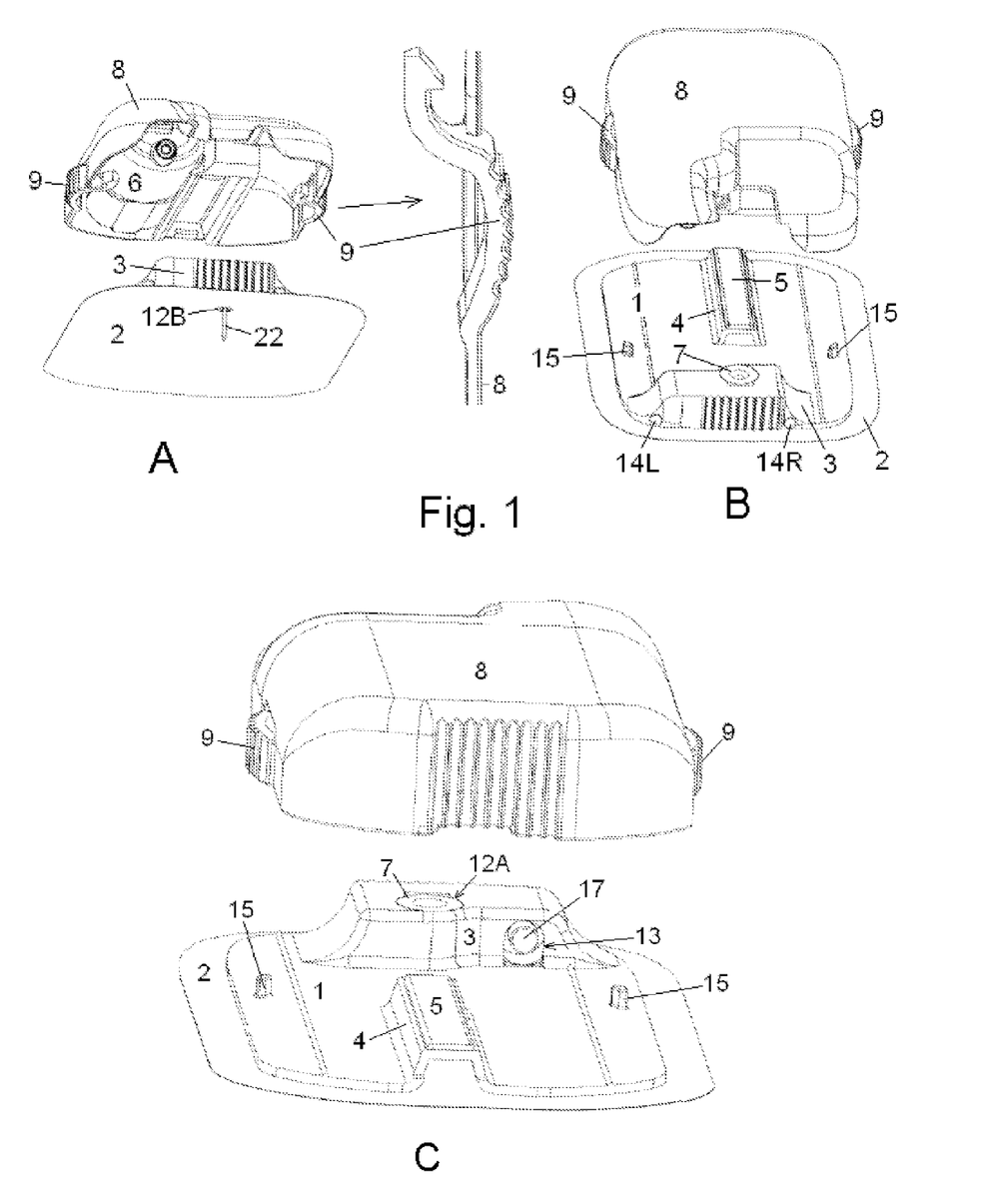

As described for the known embodiment of FIG. 1 the surface plate 1 has a contact surface which is defined as the surface which is in contact with the first surface of the adhesive pad 2 which is the surface of the adhesive pad 2 facing the surface plate 1. The contact surface of the surface plate 1 and the first side of the adhesive pad 2 has areas unreleasably secured to each other by welding. Further the second surface of the adhesive pad 2 i.e. the surface facing the skin of the patient has areas provided with a skin compatible adhesive. Normally the full surface of the second surface of the adhesive pad 2 will be adhesive except for the areas which have been subjected to welding when joining the surface plate 1 and the adhesive pad 2 together as welding ruins the adhesive surface opposite the welded surfaces.

FIG. 2A-2D shows an embodiment of a base part to which it is possible to join a delivery device; the base part comprises a surface plate 1 and an adhesive part 2.

FIG. 2A shows the surface plate 1 separated from the adhesive pad 2 although the two parts will be joined together by welding during manufacturing. The welding positions 32 are shown on the surface plate 1 and can be seen in FIGS. 2B, 2C and 2D where the surface plate 1 is seen from below. A first welding position is placed around the opening 12B through which the cannula part 7 enters. The welding is placed in a minimum distance from the cannula opening 12B in order assure that the welding will not ruin the ability of the adhesion pad 2 to adhere to the patients skin close to the opening 12B. The distance between the edge of the opening 12B and the edge of the welding 32 should be at least 2 mm, preferably at least 3 mm, i.e. leaving at least 2 mm, preferably at least 3 mm, of unspoiled adhesive surface on the second surface of the adhesive pad 2 but generally the adhesion between to given materials such as skin and skin compatible adhesive will be improved if the common adhesive surface is large i.e. the larger the better.

Further, the surface plate 1 has a welding position 32 close to the opposite end of the surface plate 1. This welding position 32 is shaped as a mouth or a crescent moon. The function of this rather large welding is to assure that the surface plate 1 will not pivot around the welding and/or other fastening means positioned at the opposite end i.e. the "cannula" end, but will be firmly positioned relative to the adhesive pad 2.

The reference numbers of FIG. 2A refers to similar parts with same numbers as described in FIG. 1A-1C, "similar parts" are parts with same function although not with exactly the same look.

The surface plate 1 of this embodiment is rather large and rigid. That the surface plate is large means that it has a dimension which is more than 3 cm long e.g. the diameter should be at least 3 cm for a round surface plate 1, when the surface plate 1 has credit card size it has a length of at least 8 cm and a width of at least 4 cm, the adhesive pad 2 will be larger than the contact surface of the surface plate, normally the adhesive pad 2 will extend the contact surface with at least 3 mm in all directions i.e. if the contact surface is round and have a diameter of 4 cm the diameter of a round adhesive pad 2 would be at least 4.6 cm and the length/width of a square adhesion pad 2 would be at least 4.6 cm.

The adhesive pad 2 of FIG. 2A-B is provided with a release liner 31; a release liner protects the adhesive surface before use but can easily be peeled of by the user before the base part is to be positioned on the patient's skin. In FIG. 2A which shows the embodiment from above it is only possible to see a handle part of the two-piece release liner 31. Also the embodiment of the base part shown in FIG. 2A is provided with an adhesive part 30 which is shown as secured to the adhesive pad 2. The adhesive part 30 can be a double coated tape. If the adhesive part 30 is placed close to the edge of the adhesive pad 2 which is normally less than 1 mm thick then it would be suitable to apply a tape approved for medial use such as e.g. the tape of type 1517 from 3M. If the adhesive part 30 is placed away from the edge of the adhesive pad 2 it is not important to use a tape approved for medical use as the patient is adequately separated from the tape. But in both cases it should be possible to sterilize the tape or coating as the whole medical device will have to be sterilized before use. Normally gamma radiation or ethylene gas is used to sterilize medical devices, while this makes it desirable that the tape or coating should be able to withstand such sterilization and be able to sustain a sufficient adhesion afterwards. Adhesive parts 30 in the form of medical grade pressure sensitive plastic, non-woven and foam adhesive tapes which are suitable for the present use can be bought commercially.

The adhesive part 30 of the embodiment in FIG. 2A-2D is rectangular and has a T-shaped opening which closely follows the edge of the opening 12B in order to keep the surface plate 1 as firmly positioned in this area as possible.

The surface plate 1 of the embodiment in FIG. 2A-D is not provided with a cannula or another subcutaneous part but the base part is provided with an opening 12A/12B which can receive a cannula or another subcutaneous part 7 and when the medical device is in use the cannula or another subcutaneous part will be positioned in this opening 12A/B.

FIGS. 2E-2G illustrate the use of spot welding when replacing larger continued weldings such as those weldings illustrated in FIGS. 2A-2D. The spot weldings can have the form of small circles or short lines. That the circle is small means that no adhesive effect between skin and pad 2 is achieved within the circle, and that a line is short means that if it was rounded to a circle, i.e. tight together at the ends, no adhesive effect between skin and pad would be achieved within the formed circle.

In FIG. 2E the adhesive pad 2 and the contact surface is provided with two circular spot weldings 32 i.e. one on each side of the opening 12B through which the subcutaneous device passes. The opening 12B is placed close to the edge of the surface plate 1 and an adhesive part 30 is placed around the opening 12B. Further the adhesive pad 2 and the contact surface is provided with two circular spot weldings 32 at the opposite end, i.e. one at each side of the contact surface in order to prevent the surface plate 1 to separate from the adhesive pad 2 and pivot away from the patients skin.

In FIG. 2F the adhesive pad 2 and the contact surface is provided with linear spot weldings 32 i.e. one on each side of the opening 12B through which the subcutaneous device passes. Like in FIG. 2E an adhesive part 30 is placed around the opening 12B. Further the adhesive pad 2 and the contact surface is provided with two linear spot weldings 32 at the opposite end, i.e. one at each side of the contact surface in order to prevent the surface plate 1 to separate from the adhesive pad 2 and pivot away from the patients skin.

In FIG. 2G the adhesive pad 2 and the contact surface is provided with two circular spot weldings 32 i.e. one on each side of the opening 12B through which the subcutaneous device passes. The opening 12B is placed around the middle of the surface plate 1 and an adhesive part 30 is placed around the opening 12B. Further the adhesive pad 2 and the contact surface is provided with two linear spot weldings 32 at each end of the surface plate 1, i.e. one at each side of the contact surface in order to prevent the surface plate 1 to separate from the adhesive pad 2 and pivot away from the patients skin at either end.

Figure 3A:
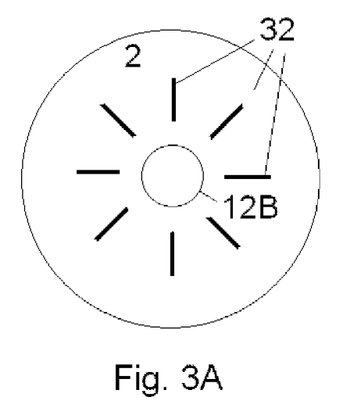
FIGS. 3A and B shows two embodiments of an adhesive pad to be used with a medical device provided with a cannula or another subcutaneously positioned part and having a contact surface facing a round adhesive pad.
Figure 3B:
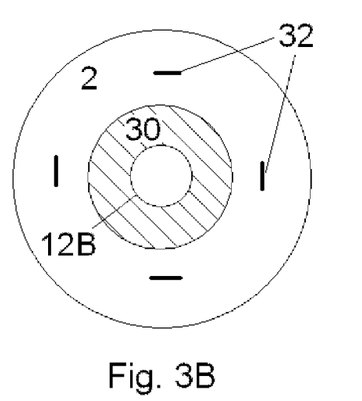

FIGS. 3A and 3B illustrates how the invention can be applied when dealing with a smaller medical device i.e. a medical device which has a contact surface smaller than 3 cm in all dimensions parallel to the skin of the patient. The shown embodiments of the adhesive pads 2 are both round having a central opening 12B which makes it possible to insert a subcutaneous part through the adhesive pad 2.

FIG. 3A illustrates an embodiment of the prior art where welding positions 32 (illustrated by 8 fat lines) often are positioned as rays extending from the center to the perimeter at the area between the contact surface of the surface plate 1 and the first surface of the adhesive pad 2. This embodiment assures a very firm attachment between the adhesive pad 2 and the surface plate 1.

FIG. 3B illustrates an embodiment according to the invention where welding positions 32 (illustrated by 4 fat lines) will placed along the edge of the contact surface of the surface plate 1 when the surface plate 1 has been secured to the adhesive pad 2. It is obvious that this embodiment will provide a much large area of adhesion between the adhesive pad 2 and the patient's skin as a smaller area of the adhesive surface will be destroyed by welding. The central opening 12B is surrounded by an adhesive part 30 which will provide adequate adhesion between the surface plate 1 and the adhesive pad 2 despite the smaller welded area.

The invention claimed is:

1. A medical device comprising:
a cannula or another part to be positioned subcutaneously when in use,
a surface plate provided with a contact surface and with an opening through which the cannula or another subcutaneously positioned part passes when the medical device is in use,
an adhesive pad secured to the contact surface of the surface plate providing adhesion of the surface plate to a skin surface, the adhesive pad comprising:
a first surface facing the contact surface and having areas unreleasably secured to the contact surface by welding, and
a second surface facing the skin of a patient during use and having areas provided with a skin compatible adhesive which can be releasably secured to the skin of a patient, and
an adhesive part placed between the contact surface of the surface plate of the medical device and the first surface of the adhesive pad in an area where the two surfaces have not been welded together thereby securing the unwelded areas of the contact surface to the first surface with the adhesive part together,
wherein the adhesive part is positioned along an edge of the opening of the contact surface of the surface plate through which opening the cannula or another subcutaneously positioned part passes, and
wherein a welding is placed between the adhesive part and at least one edge of the surface plate.

2. A medical device according to claim 1, wherein the adhesive part comprises a piece of double adhesive material wherein each side of the adhesive part is provided with adhesive coating or the adhesive part comprises a coating of adhesive placed directly on the contact surface of the surface plate or the adhesive part comprises a coating of adhesive placed directly on the first surface of the adhesive pad.

3. A medical device according to claim 1, wherein the adhesive part comprises a piece of double adhesive tape which can be sterilized by either gamma radiation or ethylene oxide gas.

4. A medical device according to claim 1, wherein the adhesive part comprises a piece of double adhesive tape which can sterilized by either gamma radiation or ethylene oxide gas.

5. A medical device according to claim 1, wherein spot weldings are placed on at least two opposite sides of the adhesive part.

6. A medical device according to claim 1, wherein the welding placed between the adhesive part and the at least one edge of the surface plate comprises either a larger circular welding or one or more spot weldings.

7. A medical device according to claim 1, wherein the subcutaneously positioned part is a sensor.

8. The medical device of claim 1, comprising a second welding position at least 2 mm from the first welding position.

9. A base part of a medical device comprising:
  a surface plate provided with a contact surface and with an opening through which a cannula or another subcutaneously positioned part passes when the medical device is in use, and
  an adhesive pad secured to the contact surface of the surface plate providing adhesion of the surface plate to a skin surface, the adhesive pad comprising:
    a first surface facing the contact surface and having areas unreleasably secured to the contact surface by welding, and
    a second surface facing the skin of a patient during use and having areas provided with a skin compatible adhesive which can be releasably secured to the skin of a patient, and
  an adhesive part placed between the contact surface of the surface plate of the base part and the first surface of the adhesive pad in an area where the two surfaces have not been welded together thereby securing the unwelded areas of the contact surface to the first surface with the adhesive part,
    wherein the adhesive part is positioned along an edge of the opening of the contact surface of the surface plate through which opening the cannula or another subcutaneously positioned part passes, and
    wherein a welding is placed between the adhesive part and at least one edge of the surface plate.

10. An adhesive pad secured to a medical device and providing adhesion of the medical device to a skin surface, the adhesive pad comprising:
  a first surface facing the medical device having areas unreleasably secured to the medical device by welding,
  a second surface having areas provided with a skin compatible adhesive which can be releasably secured to the skin of a patient, wherein the first surface has at least one area provided with an adhesive part securing the first surface to the medical device, and
  an opening for a cannula or another subcutaneously positioned part to pass through,
    wherein the adhesive part is positioned along an edge of the opening, and
    wherein a welding is placed between the adhesive part and at least one edge of the first surface.

* * * * *